US00PP19194P2

(12) United States Plant Patent
Hofmann

(10) Patent No.: US PP19,194 P2
(45) Date of Patent: Sep. 9, 2008

(54) ***NEMESIA* PLANT NAMED 'INNKARWHI'**

(50) Latin Name: *Nemesia hybrida*
Varietal Denomination: Innkarwhi

(75) Inventor: Silvia Hofmann, Mainz (DE)

(73) Assignee: Innovaplant GmbH & Co., Gensingen (DE)

( * ) Notice: Subject to any disclaimer, the term of this patent is extended or adjusted under 35 U.S.C. 154(b) by 0 days.

(21) Appl. No.: 11/800,794

(22) Filed: May 7, 2007

(51) Int. Cl.
*A01H 5/00* (2006.01)

(52) U.S. Cl. ..... Plt./458; Plt./263.1
(58) Field of Classification Search ..... Plt./458
See application file for complete search history.

(56) References Cited

PUBLICATIONS

UPOV–ROM GTITM Plant Variety Database, 2007/05, GTI Jouve Retrieval Software, citation for 'Innkarwhi' (country—Canada (CA)).*
UPOV–ROM GTITM Plant Variety Database, 2007/05, GTI Jouve Retrieval Software, citation for 'Innkarwhi' (country—The European Community (QZ)).*

* cited by examiner

*Primary Examiner*—Kent L. Bell
*Assistant Examiner*—S. B. McCormick-Ewoldt
(74) *Attorney, Agent, or Firm*—C. A. Whealy

(57) ABSTRACT

A new and distinct variety of *Nemesia* plant named 'Innkarwhi', characterized by its compact, upright and rounded growth habit; vigorous growth habit; freely flowering habit; white-colored flowers; and strongly fragrant flowers.

1 Drawing Sheet

Botanical designation: *Nemesia hybrida.*
Cultivar denomination: 'Innkarwhi'.

BACKGROUND OF THE INVENTION

The present invention relates to a new and distinct cultivar of *Nemesia,* botanically known as *Nemesia hybrida* and hereinafter referred to by the name 'Innkarwhi'.

The new *Nemesia* is a product of a planned breeding program conducted by the Inventor in Gensingen, Germany. The objective of the breeding program is to create new uniform *Nemesia* cultivars with fragrance and attractive flower coloration.

The new *Nemesia* originated from a cross-pollination during the summer of 2001 in Gensingen, Germany of a proprietary selection of *Nemesia hybrida* identified as code number N01 2-4, not patented, as the female, or seed parent with a proprietary selection of *Nemesia hybrida* identified as code number N01 4-3 tet 4, not patented, as the male, or pollen, parent. The new *Nemesia* was discovered and selected by the Inventor as a single flowering plant within the progeny of the stated cross-pollination in a controlled environment in Gensingen, Germany during the spring of 2001.

Asexual reproduction of the new *Nemesia* by terminal cuttings in a controlled environment in Gensingen, Germany since the spring of 2002, has shown that the unique features of this new *Nemesia* are stable and reproduced true to type in successive generations.

SUMMARY OF THE INVENTION

The cultivar Innkarwhi has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Innkarwhi'. These characteristics in combination distinguish 'Innkarwhi' as a new and distinct cultivar of *Nemesia:*

1. Compact, upright and rounded growth habit.
2. Vigorous growth habit.
3. Freely flowering habit.
4. White-colored flowers.
5. Strongly fragrant flowers.

Plants of the new *Nemesia* differ from plants of the female parent selection primarily in growth habit as plants of the female parent selection have longer internodes than plants of the new *Nemesia.* In addition, plants of the new *Nemesia* do not produce seeds whereas plants of the female parent selection produce seeds.

Plants of the new *Nemesia* differ from plants of the male parent selection primarily in growth habit as plants of the male parent selection have longer internodes than and are not as freely branching as plants of the new *Nemesia.*

Plants of the new *Nemesia* can be compared to plants of the cultivar Imprinno, not patented. In side-by-side comparisons conducted by the Inventor in Gensingen, Germany, plants of the new *Nemesia* differed from plants of the cultivar Imprinno in the following characteristics:

1. Plants of the new *Nemesia* were more vigorous and stronger than plants of the cultivar Imprinno.
2. Plants of the new *Nemesia* had shorter internodes than plants of the cultivar Imprinno.

BRIEF DESCRIPTION OF THE PHOTOGRAPHS

The accompanying colored photographs illustrate the overall appearance of the new *Nemesia,* showing the colors as true as it is reasonably possible to obtain in colored reproductions of this type. Colors in the photographs may differ slightly from the color values cited in the detailed botanical description which accurately describe the colors of the new *Nemesia*.

The photograph at the bottom of the sheet comprises a side perspective view of a typical flowering plant of 'Innkarwhi' grown in a container.

The photograph at the top of the sheet is a close-up view of typical flowers of 'Innkarwhi'.

DETAILED BOTANICAL DESCRIPTION

The aforementioned photographs and following observations, measurements and values describe plants grown in Bonsall, Calif. in containers in an outdoor nursery during the summer and under conditions which closely approximate commercial production. During the production of the plants, day temperatures ranged from about 18° C. to 38° C. and night temperatures ranged from about 16° C. to 24° C. Plants were pinched one time and were about nine weeks old when the photographs and the description were taken. In the description, color references are made to The Royal Horticultural Society Colour Chart, 1995 Edition, except where general terms of ordinary dictionary significance are used.

Botanical classification: *Nemesia hybrida* cultivar Innkarwhi.

Parentage:

*Female, or seed, parent.*—Proprietary selection of *Nemesia hybrida* identified as code number N01 2-4, not patented.

*Male, or pollen, parent.*—Proprietary selection of *Nemesia hybrida* identified as code number N01 4-3 tet 4, not patented.

Propagation:

*Type.*—By terminal cuttings.

*Time to initiate roots, summer.*—About ten days at 20° C.

*Time to initiate roots, winter.*—About two weeks at 20° C.

*Time to produce a rooted young plant, summer.*—About two weeks at 20° C.

*Time to produce a rooted young plant, winter.*—About two to three weeks at 20° C.

*Root description.*—Fine; white in color.

*Rooting habit.*—Freely branching.

Plant description:

*Plant and growth habit.*—Compact, upright and rounded growth habit. Vigorous growth habit. Relatively short internodes. Freely branching; about eight to ten primary branches develop per plant with numerous secondary and tertiary laterals.

*Plant height.*—About 32 cm.

*Plant diameter.*—About 35 cm.

Lateral branch description:

*Length.*—About 28 cm.

*Diameter.*—About 2.5 mm.

*Internode length.*—About 2.6 cm.

*Strength.*—Strong.

*Aspect.*—Mostly upright to slightly outwardly slanting.

*Texture.*—Smooth, glabrous.

*Color.*—144A.

Foliage description:

*Arrangement.*—Opposite, simple.

*Length.*—About 4.1 cm.

*Width.*—About 2.3 cm.

*Shape.*—Ovate.

*Apex.*—Acute.

*Base.*—Attenuate.

*Margin.*—Serrate.

*Texture, upper and lower surfaces.*—Smooth, glabrous.

*Venation pattern.*—Pinnate; arcuate.

*Color.*—Developing foliage, upper surface: Darker than 138A. Developing foliage, lower surface: 146B. Fully expanded foliage, upper surface: 147A; venation, 146B. Fully expanded foliage, lower surface: 147B; venation, 146B.

*Petiole length.*—About 3 mm.

*Petiole diameter.*—About 3 mm.

*Petiole texture, upper and lower surfaces.*—Smooth, glabrous.

*Petiole color, upper and lower surfaces.*—144A.

Flower description:

*Flower arrangement and habit.*—Zygomorphic solitary flowers arranged on terminal racemes; flowering acropetally towards the apex. Flowers bilabiate. Flowers face upright to outwardly. Flowers last about three to four days on the plant. Flowers not persistent. Freely flowering habit with about 14 to 15 flowers per inflorescence and about 100 open flower and flower buds developing per lateral branch.

*Fragrance.*—Strong; sweet, pleasant, vanilla-like.

*Natural flowering season.*—In Germany, plants flower from May through September; flowering continuous during this period.

*Inflorescence height.*—About 4.5 cm to 5 cm.

*Inflorescence diameter.*—About 4 cm.

*Flower diameter.*—About 1.5 cm.

*Flower length.*—About 1.8 cm.

*Flower depth.*—About 1 cm.

*Flower buds.*—Length: About 1 cm. Diameter: About 1.1 cm. Shape: Obovate. Color: 155D.

*Petals.*—Arrangement: Five petals; four upper petals fused at base to form an upright lobed and arched upper or banner lip; lower petal modified into a large lip with convex oval protuberance and nectar spur. Shape: Oval to obovate. Apex: Rounded. Margin: Entire. Length: Center upper petals: About 7 mm. Lateral upper petals: About 6 mm. Lower petal: About 8 mm. Width: Center upper petals: About 4 mm. Lateral upper petals: About 6 mm. Lower petal: About 1.4 cm. Texture, upper and lower surfaces: Smooth, glabrous. Color: When opening, upper and lower surfaces: Close to 155D. Fully opened, upper surface: Close to 155D; protuberance, close to 14B. Fully opened, lower surface: Close to 155D; nectar spur, close to 157B.

*Sepals.*—Arrangement: Calyx star-shaped with five sepals fused at the base. Shape: Elliptic. Apex: Acute. Margin: Entire. Length: About 4 mm. Width: About 2 mm. Texture, upper and lower surfaces: Pubescent. Color, upper surface: 146A. Color, lower surface: 146B.

*Peduncles.*—Length: About 3 cm. Diameter: About 1.5 cm. Angle: Erect. Strength: Strong. Texture: Pubescent. Color: 146A.

*Pedicels.*—Length: About 1.5 cm. Diameter: About 1 mm. Angle: About 30° to 45° from peduncle axis. Strength: Strong. Texture: Pubescent. Color: 146B.

*Reproductive organs.*—Stamens: Quantity/arrangement: Four per flower. Filament length: About 1 mm to 3 mm. Filament color: Close to 155D. Anther shape: Oval. Anther length: Less than 1 mm. Anther color: 12B. Pollen amount: Scarce. Pollen color: 12C. Pistils: Quantity: One per flower. Pistil length: About 3 mm. Style length: About 1 mm. Style color: 145C. Stigma shape: Rounded. Stigma color: 145C. Ovary color: 145A. Seed/fruit: Seed and fruit development have not been observed on plants of the new *Nemesia.*

Pathogen/pest resistance: Plants of the new *Nemesia* have not been observed to be resistant to pests and pathogens common to *Nemesia.*

Garden performance: Plants of the new *Nemesia* have been observed to tolerate wind and rain and have good garden performance.

Temperature tolerance: Plants of the new *Nemesia* have been observed to tolerate temperatures from about 5° C. to about 35° C.

It is claimed:

1. A new and distinct *Nemesia* plant named 'Innkarwhi' as illustrated and described.

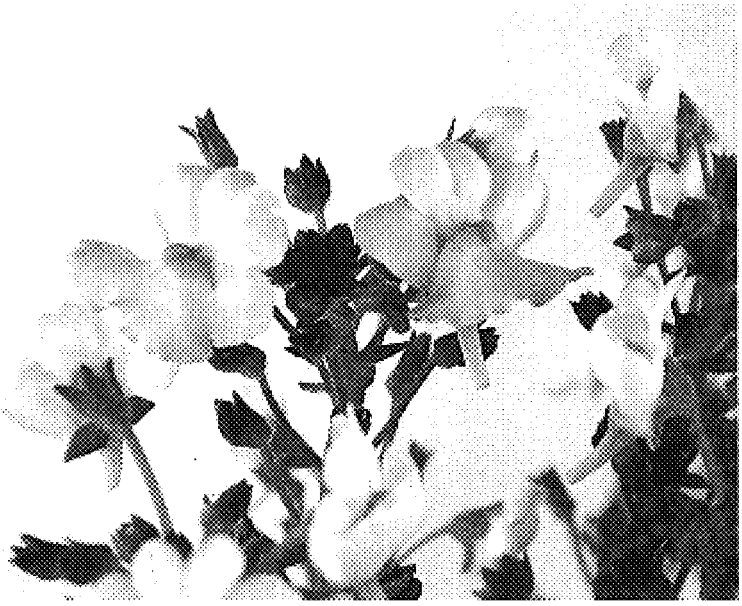
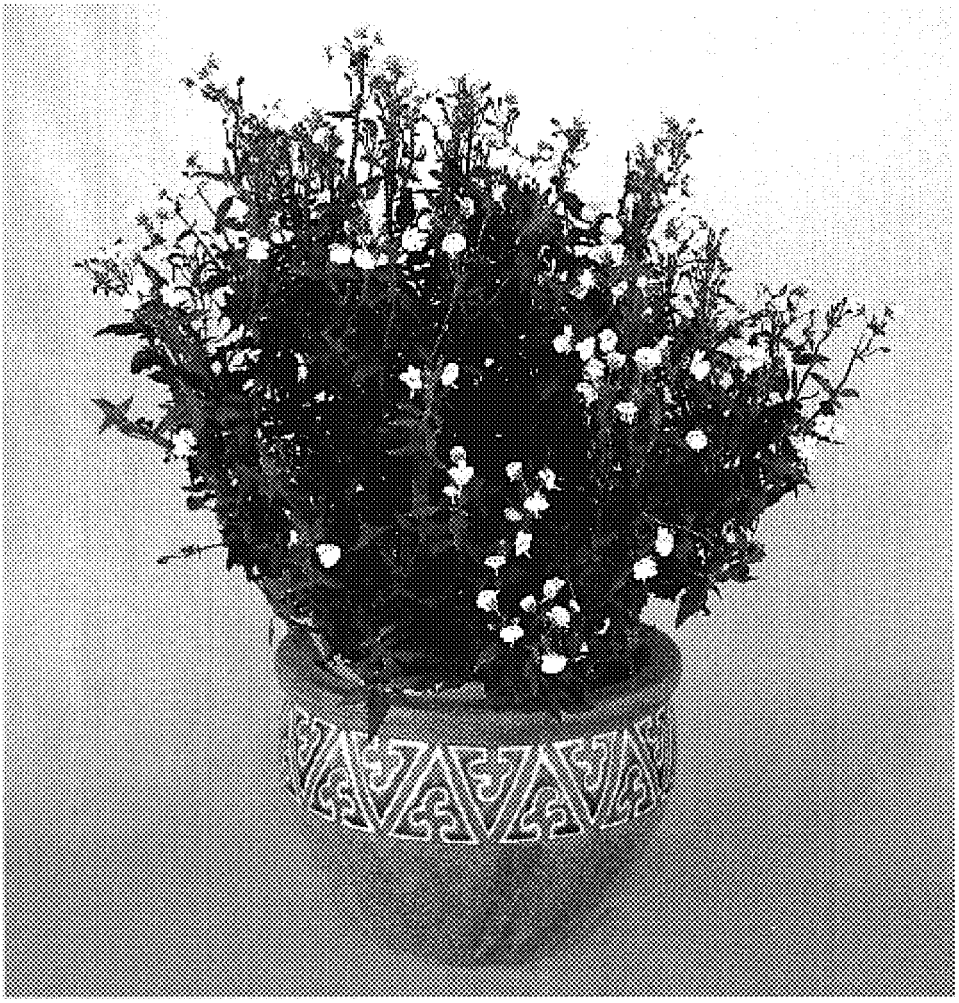

* * * * *